United States Patent [19]

Falb et al.

[11] Patent Number: 5,242,403
[45] Date of Patent: Sep. 7, 1993

[54] PUMPING DEVICE FOR THE METERED FEED OF LIQUIDS

[75] Inventors: Wolfgang Falb, Krummesse; Karl-Ludwig Gippert; Ulrich Heim, both of Lübeck; Uvo Hölscher, Stockelsdorf; Siegfried Kiske, Gross Grönau; Götz Kullik, Lübeck; Ralf-Ernst Löser, Kreuzkamp; Christoph Maurer, Bad Schwartau, all of Fed. Rep. of Germany

[73] Assignee: Drägerwerk Aktiengesellschaft, Lübeck, Fed. Rep. of Germany

[21] Appl. No.: 833,329

[22] Filed: Feb. 10, 1992

[30] Foreign Application Priority Data

Mar. 28, 1991 [DE] Fed. Rep. of Germany ....... 4110253

[51] Int. Cl.⁵ ................................................ A61F 7/12
[52] U.S. Cl. ..................................... 604/113; 62/3.2; 62/47.1; 62/50.6; 128/204.15; 417/313; 417/572
[58] Field of Search ................... 417/313, 572; 62/3.2, 62/50.6, 47.1; 604/113, 114; 128/203.26, 204.15

[56] References Cited

U.S. PATENT DOCUMENTS 4,405,294  9/1983  Albarda ........................... 417/488

FOREIGN PATENT DOCUMENTS 1374710  8/1964  France .

Primary Examiner—Ronald C. Capossela
Attorney, Agent, or Firm—McGlew and Tuttle

[57] ABSTRACT

A metering pump for metering low-boiling liquids, especially liquid anesthetics provides continuous metering of liquid. To achieve this, the pump chamber 7 is maintained at a temperature below the boiling point of the liquid by means of a cooling device 14, preferably a Peltier cell.

15 Claims, 1 Drawing Sheet

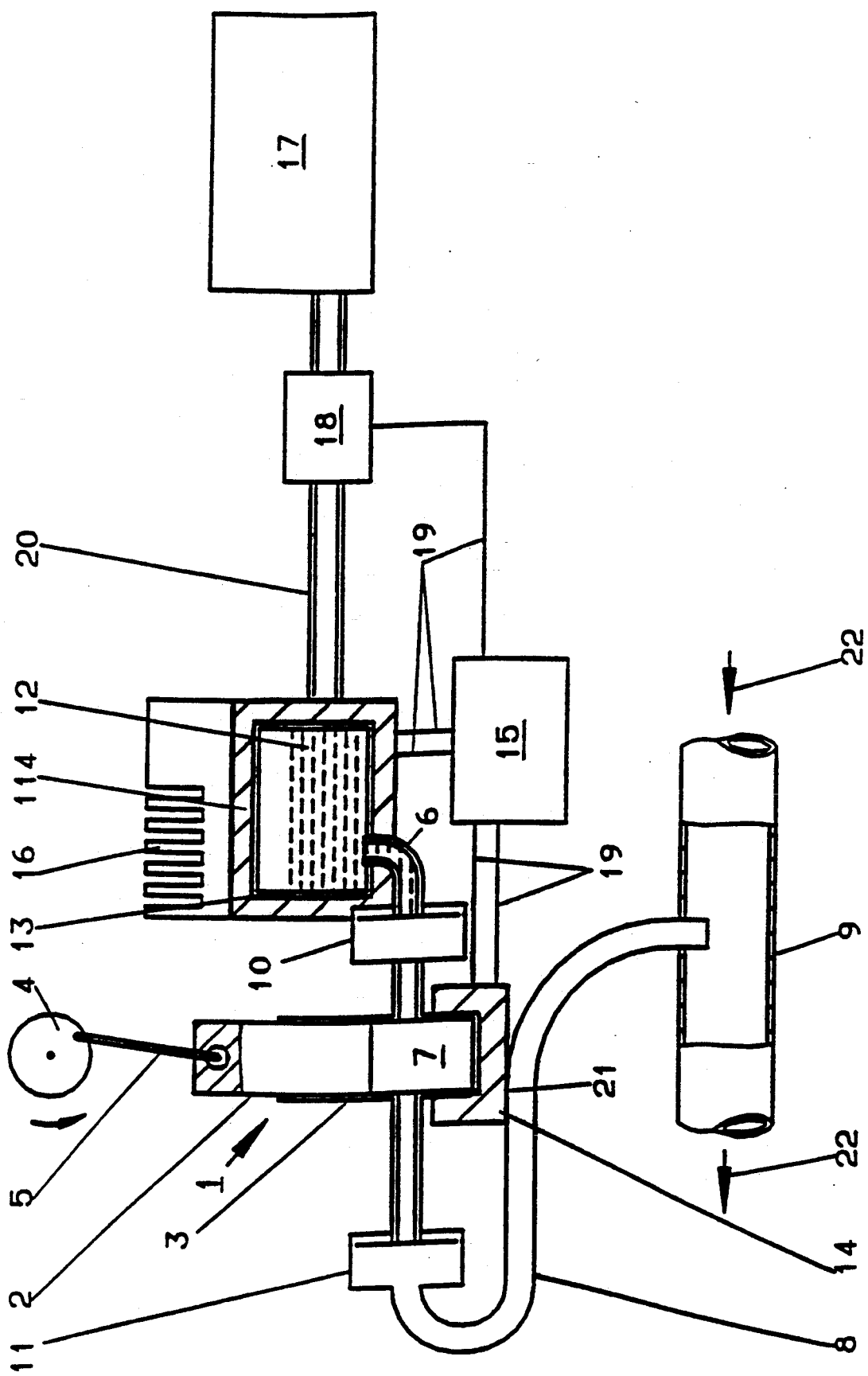

PUMPING DEVICE FOR THE METERED FEED OF LIQUIDS

FIELD OF THE INVENTION

The present invention pertains generally to a pumping device for the metered feed of liquids and more particularly to metered feed by pump strokes from a reservoir via a feed line into a pump chamber and from there to a user via a discharge line for performing anesthesia.

BACKGROUND OF THE INVENTION

Such a pumping device has become known from U.S. Pat. No. 4,405,294 (corresponding to German Offenlegungsschrift No. DE-OS 30,38,525).

The prior-art metering pump is designed as a reciprocating piston pump which delivers defined, adjustable delivery volumes from a feed line into a discharge line and from there to a user during the pump stroke.

Such metering pumps are used for the highly accurate, reproducible feed of liquids which are needed especially in medical engineering for performing anesthesia. It is important to maintain the amounts metered as accurately and reproducibly as possible in order to subsequently feed anesthetic to be evaporated into a carrier gas stream and thus to reach an anesthetic concentration in the carrier gas that is determined by the metering pump. However, it was found that especially in the case of low-boiling anesthetics, the feed strokes increasingly generate a vacuum in the liquid, so that gas bubbles are formed and undesirably entrained, which jeopardizes the accuracy of metering. In addition, readily boiling liquids are able to produce considerable amounts of gas in the feed lines, which make continuous metering of liquid impossible, even at room temperature.

SUMMARY AND OBJECTS OF THE INVENTION

It is a primary object of the present invention to improve a metering pump of the above-described class so that continuous metering of liquids becomes possible even in the case of low-boiling liquids.

This object is attained by maintaining the pump chamber located between the feed line and the discharge line at a temperature below the boiling point of the liquid by means of a cooling device.

The present invention achieves essentially the advantage that bubble formation within the boiling liquid does not play any role any longer at the decisive moment of the delivery process in the pump, because the gas present in the pump is returned into the liquid phase by condensation, and it is thus ensured that liquid is present in the pump chamber at any point in time of the feed stroke. The temporary vacuum generated during a suction stroke is also unable to lead to bubble formation in the liquid. Setting the temperature in the pump chamber below the boiling point permits reliable operation regardless of the actual atmospheric pressure (altitude). The cooling device may consist of, e.g., a Peltier cell whose cold surface is in thermal contact with the pump chamber and whose warm surface is in connection with the surroundings via a cooling body.

The reservoir and the feed line are preferably brought into thermal contact with a cooling device. This cooling device may also be a Peltier cell which surrounds the reservoir at least partially and whose cool surface forms a closed surface around the vessel wall. The feed line as well as the liquid-carrying lines opening into the reservoir are made of a material with good thermal conductivity, so that the cooled surface on the reservoir and on the pump chamber also ensures good cooling of the line connections at the same time, without separate cooling devices being provided at these points. Ceramic materials can be considered to be materials with good thermal conductivity in this sense. The cooling of the reservoir also shows the advantage that the cooling energy can be distributed over a larger area, so that the necessary heat dissipation does not cause any major problems.

If cooling of the reservoir is to be eliminated, it is favorable to design the reservoir as a pressure-resistant vessel. By this design the low-boiling liquid is able to build up a vapor pressure in the reservoir, at a corresponding ambient temperature above the boiling point, which prevents further evaporation of the liquid. In this case, the liquid is fed under excess pressure from the reservoir into the pump, in whose pump chamber it will then be cooled to a temperature below the boiling point. Cooling of the feed line may also be eliminated in this case. To eliminate the need to store large amounts of liquids in the cooled state and to save cooling energy, it is advantageous to provide in the feed line a reservoir designed as a storage space, which can be refilled from a supply vessel as needed. The capacity of the storage space may be kept so small that it contains at least slightly more than the amount of a reserve needed for one metering stroke. As a result, the amount of liquid to be cooled is limited to the absolutely necessary amount.

If a Peltier cell is used as the cooling device for the pump chamber, it is advantageous to bring the discharge line into thermal contact with its warm surface facing away from the pump chamber. Such an arrangement is favorable especially when an anesthetic boiling at room temperature is used as the liquid to be metered, which is metered in the cooled state as a liquid, but is subsequently to be metered as an anesthetic gas into a carrier gas line in which it is to be united with an anesthetic gas (oxygen-laughing gas mixture). The heat released by the Peltier cell during cooling is now also used to transform the anesthetic being pumped in the liquid state into the gaseous state instead of releasing this heat into the surroundings.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which a preferred embodiment of the invention is illustrated.

BRIEF DESCRIPTION OF THE DRAWINGS

In the drawings:

The only FIGURE is a schematic partially sectional view of the metering pump system according to the invention.

DETAILED DESCRIPTION OF THE PREFERRED EMBODIMENT

The only FIGURE shows a metering pump 1, in which a pump piston 2 is arranged displaceably in a pump cylinder 3 via an eccentric drive 4 and an eccentric connecting rod 5. A feed line 6 opens into the pump chamber 7, from which a discharge line 8 opens into an anesthetic gas line 9, only part of which is shown. The feed line 6 is provided with an intake valve 10, and the discharge line 8 is provided with a discharge valve 11. Both valves 10, 11 act as directional valves for the inflow of a liquid anesthetic 12 from a reservoir 13 into the pump chamber 7, and from there into the discharge line 8. The pump chamber 7 is provided with a cooling device 14 designed as a Peltier cell, which, being in contact with the outer wall of the pump chamber 7, is in thermal contact with it. Part of the discharge line 8 is led along the surface 21 of the cooling device 14 facing away from the pump chamber 7. The reservoir 13 is also provided with a cooling device 114, which is composed of a number of Peltier cells. Both the cooling devices 14, 114 are supplied with the energy necessary for their operation from an electrical power supply unit 15. The cooling device 114 around the reservoir 13 is equipped with a cooling body 16. The liquid anesthetic 12 is kept ready in a supply vessel 17, from which it is pumped by means of a feed pump 18 into the reservoir 13 as needed. The point in time for resupplying the reservoir 13 with the liquid anesthetic 12 is determined by monitoring the filling level in the reservoir 13 by means of a filling level indicator, not shown. The cooling devices 14, 114 and the feed pump 18 are supplied with electricity from the power supply unit 15 via electrical supply lines 19.

To operate the metering pump, the reservoir 13 is first filled with the anesthetic 12 by pumping a corresponding amount from the supply vessel 17 into the interior space of the reservoir 13 by means of the feed pump 18. When the desired filling level in the reservoir 13 is reached, the feed pump 18 is turned off, and the eccentric drive 4 actuates the pump piston 2 to perform feed strokes of the metering pump 1. Since the anesthetic 12 in the reservoir 13 is cooled to below its boiling point by means of the cooling device 114, a quantity being delivered of the liquid anesthetic 12 is transported into the pump chamber 7 via the opening intake valve 10. The extension of the pump chamber 7 is reduced during the subsequent pump stroke of the pump piston 2, and the excess pressure now generated opens the discharge valve 11 and closes the intake valve 10. Because of the cooling device 14, the anesthetic 12 remains in its liquid state during the entire pumping process and is fed as a liquid into the discharge line 8. On its way to the anesthetic gas line 9, the liquid anesthetic is sent past the warm surface 21 of the cooling device 14, and the heat released by the Peltier cell of the cooling device 14 is transferred to the liquid anesthetic because of the thermal contact; the liquid anesthetic is heated, and transformed into the vapor form. This pumping process is repeated until the liquid level of the anesthetic 12 in the reservoir 13 has dropped to the liquid level monitored by the filling level indicator. As soon as this level is reached, the filling level indicator sends a signal to the power supply unit 15, after which the latter puts the feed pump 18 into operation in order to raise the filling level of the anesthetic 12 again.

The gaseous anesthetic being fed enters from the discharge line 8 into the anesthetic gas line 9, through which an anesthetic gas flows in the direction of the flow arrows 22.

While a specific embodiment of the invention has been shown and described in detail to illustrate the application of the principles of the invention, it will be understood that the invention may be embodied otherwise without departing from such principles.

What is claimed is:

1. A pumping device for the metered feed of liquid anesthetic having a boiling point below or near room temperature, comprising:
   a supply vessel containing liquid anesthetic at ambient temperature;
   a reservoir having a reservoir space of a defined size for containing the liquid anesthetic;
   feed pump means for supplying the liquid anesthetic from the supply vessel to the reservoir to substantially maintain said space of a defined size filled with the liquid anesthetic;
   a feed line connecting the reservoir to a pump chamber;
   a discharge line connecting said pump chamber to an anesthetic gas line; and
   cooling means for maintaining the pump chamber and the reservoir space at a temperature below the boiling point of the liquid.

2. A pumping device according to claim 1, wherein said reservoir and said feed line are in thermal contact with said cooling device.

3. A pumping device according to claim 1, wherein said reservoir is designed as a pressure-resistant vessel.

4. A pumping device according to claim 1, wherein said reservoir forms a storage space incorporated in said feed line, said storage space being filled up from said supply vessel as needed.

5. A pumping device according to claim 1, wherein said cooling means includes a Peltier cell disposed on said pump chamber, said discharge line being positioned in thermal contact with a warm surface of said Peltier cell, facing away from said pump chamber.

6. A pumping device according to claim 1, wherein said defined size of said reservoir space is smaller than a liquid anesthetic space defined by said supply vessel and said defined size for said reservoir space is larger than said pump chamber.

7. A pumping device for a metered feed of a liquid anesthetic, comprising:
   a supply vessel containing liquid anesthetic at ambient temperature;
   a pump chamber connected to a feed line and connected to a discharge line;
   a reservoir for supplying liquid to said pump chamber via said feed line;
   feed pump means, connected to said supply vessel and connected to said reservoir for filling said reservoir to a predetermined level with liquid anesthetic from said supply vessel;
   cooling means for maintaining said pump chamber at a temperature below the boiling point of said liquid anesthetic and for maintaining said reservoir at a temperature below the boiling point of said liquid anesthetic; and
   an anesthetic gas line, said discharge line being connected to said anesthetic gas line.

8. A pumping device according to claim 7, wherein said feed line is in thermal contact with said cooling means.

9. A pumping device according to claim 7, wherein said reservoir is designed as a pressure-resistant vessel.

10. A pumping device according to claim 7, wherein said cooling means includes a Peltier cell positioned on said pump chamber, said discharge line being positioned in thermal contact with a warm surface of said Peltier cell, facing away from said pump chamber.

11. A pumping device according to claim 7, wherein said reservoir defines a reservoir volume which is smaller than a liquid anesthetic volume of said supply vessel and larger than a volume of said pump chamber.

12. A pumping device for metered feed of liquid anesthetic having a boiling point below or near room temperature, comprising:

a supply vessel containing the liquid anesthetic at ambient temperature;

a liquid anesthetic reservoir for temporary storage of liquid anesthetic;

a liquid anesthetic connection line connecting said supply vessel to said reservoir;

a feed pump in said liquid anesthetic connection line for maintaining liquid anesthetic in said reservoir up to a desired filling level;

a feed line connected to said reservoir;

piston metering means, connected to said reservoir via said feed line, for metering desired amounts of liquid anesthetic, said piston metering means including a pump chamber;

an anesthetic gas line;

a discharge line connecting said pump chamber to said anesthetic gas line; and cooling means for maintaining said pump chamber at a temperature below the boiling point of said liquid anesthetic and for maintaining liquid anesthetic in said reservoir at a temperature below the boiling point of said liquid anesthetic.

13. A pumping device according to claim 12, wherein said cooling means includes a Peltier cell having a cool surface in thermal contact with said pump chamber, said Peltier cell having a warm surface facing away from said pump chamber, said discharge line being positioned in thermal contact with said warm surface of said Peltier cell.

14. A pumping device according to claim 12, wherein each of said connecting line and said feed line are made of ceramic material.

15. A pumping device according to claim 12, wherein said liquid anesthetic reservoir defines a liquid anesthetic temporary storage space sized smaller than a liquid anesthetic volume defined by said supply vessel and larger than a stroke volume of said feed pump.

* * * * *